US00PP14817P2

(12) United States Plant Patent
Heims

(10) Patent No.: US PP14,817 P2
(45) Date of Patent: May 25, 2004

(54) BRUGMANSIA PLANT NAMED 'SNOWBANK'

(50) Latin Name: *Brugmansia sp.*
Varietal Denomination: Snowbank

(75) Inventor: Daniel M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 79 days.

(21) Appl. No.: 10/452,948

(22) Filed: Jun. 2, 2003

(51) Int. Cl.[7] ..... A01H 5/00
(52) U.S. Cl. ..... Plt./226
(58) Field of Search ..... Plt./263, 226

*Primary Examiner*—Bruce R. Campell
*Assistant Examiner*—June Hwu
(74) *Attorney, Agent, or Firm*—Klarquist Sparkman, LLP

(57) ABSTRACT

The new and distinct Brugmansia plant named 'Snowbank' is characterized by its extremely showy white, wide leaf margins and large leaf size.

2 Drawing Sheets

Botanical name: *Brugmansia sp.*
Cultivar name: 'Snowbank'.

BACKGROUND OF THE INVENTION

The present invention relates to a new and distinct cultivar of Brugmansia hybrid, and given the cultivar name 'Snowbank'. Brugmansia is in the family Solanaceae.

The new cultivar origination as a mutation in tissue culture from Brugmansia 'Sunset', a variegated form of Brugmansia 'Charles Grimaldi'. Both are unpatented plants.

This new Brugmansia hybrid is unique in its extra wide margin of white.

This plant is characterized by the following:

1. Large, beautifully variegated leaves.
2. Upright habit.
3. Large, pendulous flowers that change in color from light yellow to cream to peach.
4. Excellent vigor.
5. Fragrance.

This new cultivar has been reproduced only by asexual propagation (tissue culture). Each of the progeny exhibits identical characteristics to the original plant. Asexual propagation by tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

The following is a detailed description of the new Brugmansia selection based on observations of one-year-old specimens grown in the trial fields in Canby, Oreg. The color descriptions are all based on The Royal Horticultural Society Colour Chart.

Botanical classification: *Brugmansia hybrid.*
Cultivar name: 'Snowbank'.
Plant:
- *Form.*—Shrub.
- *Hardiness.*—U.S.D.A. Hardiness Zones 8–10.
- *Size.*—64 cm wide and 78 cm tall.

Leaf:
- *Type.*—Simple.
- *Arrangement.*—Alternate.
- *Shape.*—Broadly elliptic to ovate.
- *Blade size.*—Grows to 30 cm long and 19 cm wide.
- *Venation.*—Pinnate.
- *Margins.*—Undulate and 2 to 5 toothed near apex.
- *Apex.*—Cuspidate.
- *Base.*—Auriculate.
- *Texture.*—Soft.
- *Vestiture.*—Glandular.
- *Petiole.*—Length — 8 cm. Width — Grows to 0.6 cm. Vestiture — Puberulous. Color — Yellow Green 147D.
- *Leaf color.*—Abaxial — Shades of green in the center of the leaf, mostly Yellow Green 147A and Greyed Green 191A with patches of Yellow Green 146B and Greyed Green 191C. The margin is cream colored, Yellow Green 150D and lighter. Adaxial — Same as above.

Flower bud:
- *Size.*—3.5 cm wide and 31 cm deep.
- *Description.*—Tubular, fringed and pleated.
- *Surface.*—Glabrous.
- *Color.*—Yellow Green 1C at the base to Yellow 10A in the middle to Yellow Orange 16C at the tip.

Flower:
- *Type.*—Solitary. Perfect. Pendulous.
- *Shape.*—Funnelform, with 5 reflexed lobes.
- *Size.*—20 cm wide and 30 cm deep including fringe.

*Color.*—When opening the flower is yellow, Yellow 12B to C. When first open it is cream, Yellow 12D. When mature it is light peach, Orange 24D with a cream base, Yellow 12D.

*Corolla.*—Petal number — 5 lobes. Width — 8 cm wide at tube and 10 cm wide where inflated and 20 cm wide at fringe. Depth — 30 cm. Tube is 14 cm deep, inflated part of the tube is 10 cm deep and lobes are 5.5 cm deep when viewed from the side. Lobes — Reflexed and fringed at apices. 9 cm deep and 8 cm wide at base of lobe. Fringe is 6 cm long. Surface — Glabrous.

*Calyx.*—Sepal number — 1, spathiform. Size — 12 cm deep and 2 cm wide. The one lobe is cut 3.3 cm deep. Color — Yellow Green 147C fading to 145C with streaks of cream, Yellow White 158B.

*Stamens.*—Number — 5. Filaments — Cream colored, Yellow White 158A. 4.5 cm long from where originates on tube. Anthers — Undehisced, 3.3 cm long and Yellow White 158A. Pollen color — Yellow White 158A.

*Pedicel.*—Length — Grows to 5.5 cm. Vestiture — Pubescent. Color — Yellow Green 146C.

*Pistil.*—Size — 21 cm long. Style color — Yellow White 158A. Stigma color — Yellow White 158A.

*Fragrance.*—Heavily fragrant in evenings.

*Bloom time.*—July through September outside in Canby, Oreg.

*Lastingness.*—Each flowers lasts 3 to 5 days.

Fertility: Sterile, no fruit or seed produced.

Disease: None observed on plants grown commercially in Canby, Oreg.

COMPARISONS

Figure 1:
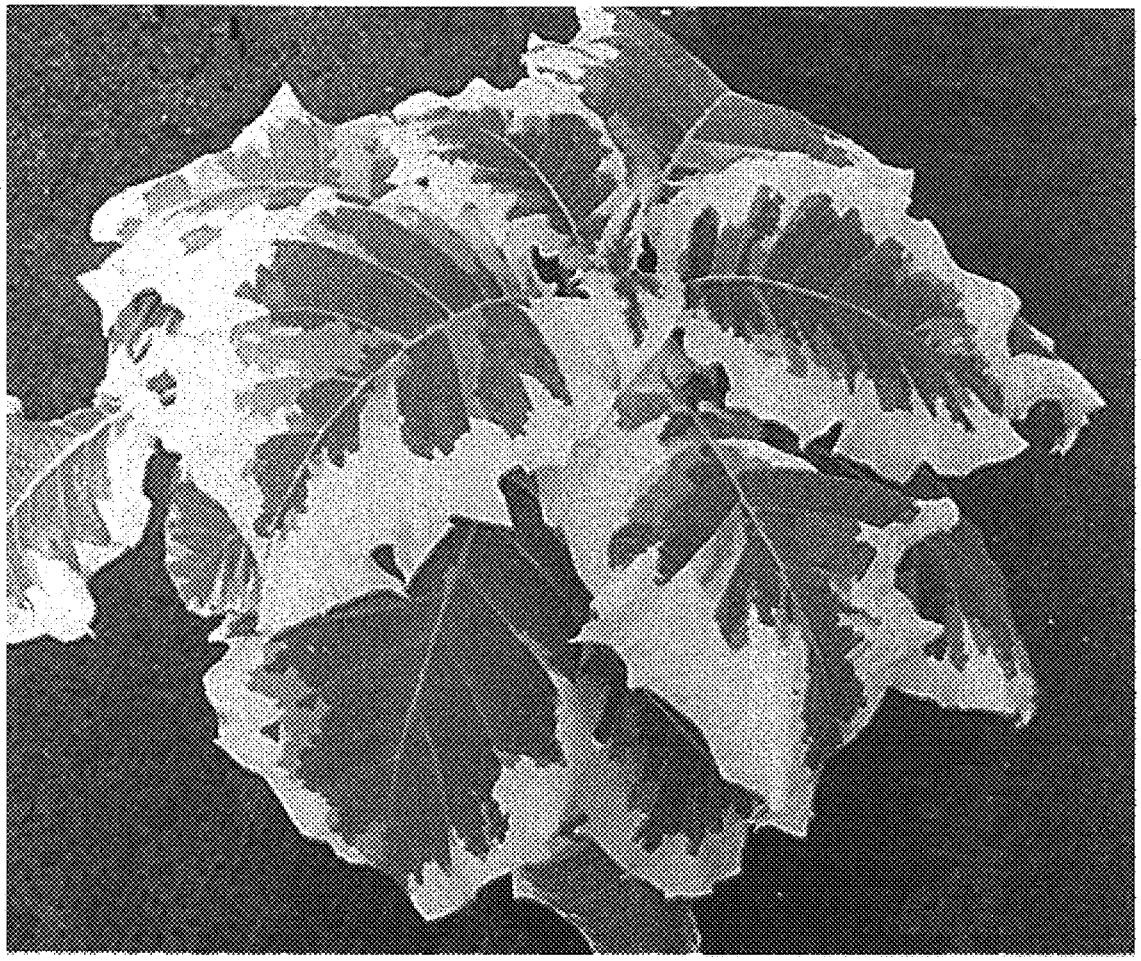
FIG. 1 shows a two year old Brugmansia 'Snowbank' growing in a two gallon pot in the greenhouse in Canby, Oreg.
Figure 2:
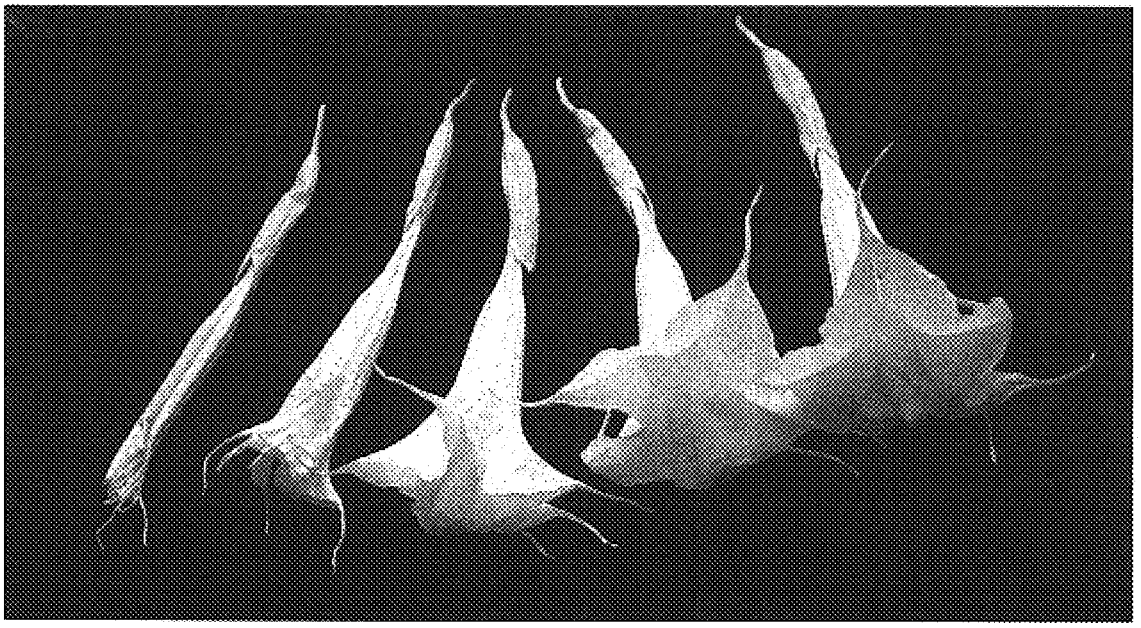
FIG. 2 shows the flower in the stages from bud to maturity.
Figure 3:
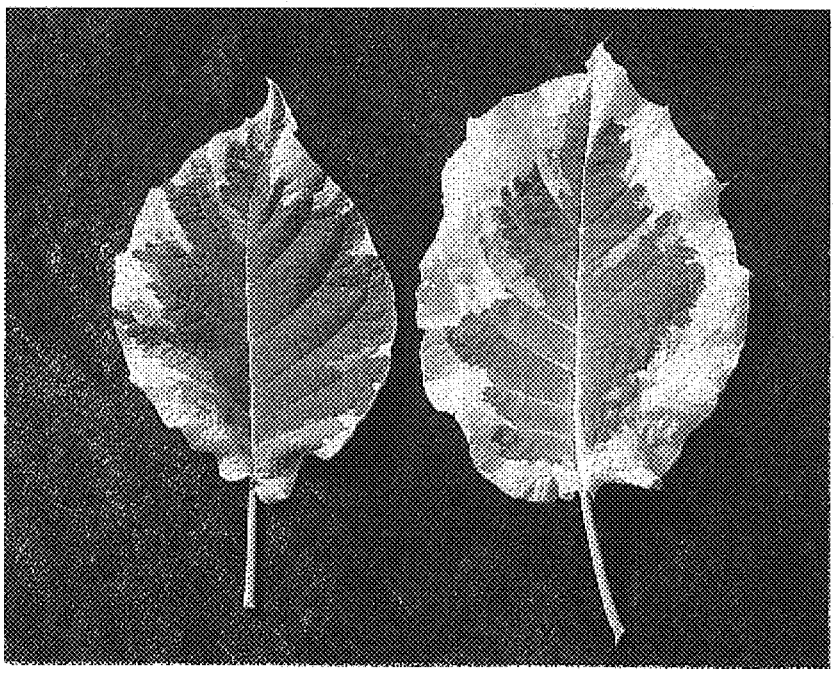
FIG. 3 shows a comparison between Brugmansia 'Snowbank' (right) and Brugmansia 'Sunset' (left).

This new cultivar is very similar in growth habit and flowering habit to Brugmansia 'Sunset' (an unpatented plant). The greatest difference is in the size of the leaf and the size of the margin. The new cultivar has a much wider margin and a larger leaf (See FIG. 3).

I claim:

1. A new and distinct cultivar of Brugmansia plant, substantially as shown and described, characterized by its extremely showy white, wide leaf margins and large leaf size.

* * * * *